United States Patent [19]

Barone

[11] 4,152,358

[45] May 1, 1979

[54] PREPARATION OF HYDROPEROXIDES BY AUTOXIDATION

[75] Inventor: Bruno J. Barone, Houston, Tex.

[73] Assignee: Petro-Tex Chemical Corporation, Houston, Tex.

[21] Appl. No.: 404,529

[22] Filed: Oct. 9, 1973

Related U.S. Application Data

[63] Continuation-in-part of Ser. No. 146,455, May 24, 1971, abandoned.

[51] Int. Cl.$^2$ ............................................ C07C 179/02
[52] U.S. Cl. .................................................... 568/568
[58] Field of Search ......................... 260/610 B, 610 A

[56] References Cited

U.S. PATENT DOCUMENTS

| | | | |
|---|---|---|---|
| 2,776,322 | 1/1957 | Webster et al. | 260/621 R |
| 2,796,439 | 6/1957 | Berneis | 260/610 B |
| 2,798,096 | 7/1957 | Baumgartner | 260/610 B |
| 2,862,973 | 12/1958 | Winkler | 260/610 |
| 3,122,417 | 2/1964 | Blaser et al. | 23/207.5 |
| 3,360,584 | 12/1967 | Kollar | 260/681 |
| 3,360,585 | 12/1967 | Winnick | 260/681 |
| 3,478,108 | 11/1967 | Creno | 260/610 |

FOREIGN PATENT DOCUMENTS 44-27022  11/1969  Japan.

OTHER PUBLICATIONS

The Merck Index, 8th Edition (1968), pp. 824–825 and 895–896; 857 and 1030.
Wazer, "Phosphorus and Its Compounds," 1958, 617–623.
The Merck Index, 8th Ed. (1968), p. 623.

*Primary Examiner*—Werren B. Lone
*Attorney, Agent, or Firm*—Kenneth H. Johnson

[57] ABSTRACT

In autoxidation of tertiary, aryl or cycloalkanes the selectivity for organic hydroperoxides can be substantially increased by using a phosphate compound of Li, Na, Mg, Ca, Sr, Fe, Cu, U or B. For example an autoxidation of isopentane with 0.05 wt. % boron phosphate at 9.9 mole % conversion gave selectivities of t-amyl hydroperoxides — 75.0 mole %, acetone — 18.3 mole % and t-amyl alcohol — 1.5 mole %. The same reaction without the phosphate at 10.0 mole % conversion gave selectivities of t-amyl hydroperoxide — 56.8 mole %, acetone — 31.2 mole % and t-amyl alcohol — 4.8 mole %.

13 Claims, No Drawings

PREPARATION OF HYDROPEROXIDES BY AUTOXIDATION

This application is a continuation in part of Ser. No. 146,455 filed May 24, 1971, now abandoned.

BACKGROUND OF THE INVENTION

The present invention relates to the preparation of the hydroperoxides of tertiary alkanes, aralkanes and cycloalkanes. More particularly it relates to the autoxidation of tertiary alkanes, aralkanes and cycloalkanes in the presence of selected phosphate compounds. The term autoxidation is understood to mean the reaction of a substance with molecular oxygen without the intervention of a flame. The hydroperoxides of tertiary, aryl and cycloalkanes have been prepared by autoxidation. Generally the results of these preparations have been rather discouraging. Two comprehensive reviews of the prior art of peroxides are "Organic Peroxides, their formation and reactions", E. G. E. Hawkins, D. Van Nostrand Company, Inc., Princeton, N.J. 1961, and "Organic Peroxides", A. G. Davies, Butterworths, London 1961, which are incorporated herein insofar as they describe the prior art.

Most known autoxidation reactions for the tertiary, aryl and cycloalkanes have relatively low selectivities for the hydroperoxides. Generally, product of such oxidations has been a mixture of oxidation products, e.g., the aldehydes, ketones, alcohols, acids, hydroperoxides, water and carbondioxide. If the desired product is a hydroperoxide then the production of such by-products and the necessity of removing some or all of them from the hydroperoxide makes an economically unattractive process. A preferable process would be one that had high selectivity for the hydroperoxide with few and relatively low concentrations of by-products. Such a process would be attractive even if low conversions were necessitated, since the hydrocarbon starting material makes an excellent diluent for the potentially dangerous hydroperoxide. Very often a product such as that described above can be used directly or with a minimum of treatment for the purification and concentration of the hydroperoxide.

It is an object of this invention to provide an improved process for the autoxidation of tertiary alkanes, aralkanes and cycloalkanes to produce hydroperoxides. It is a further object to provide a process which has high selectivity for hydroperoxides. These and other objects will become apparent from the discussion below.

SUMMARY OF THE INVENTION

It has been found that organic hydroperoxides can be obtained by a process comprising contacting a tertiary alkane, aralkane, or cycloalkane with molecular oxygen in liquid phase in the presence of a phosphate of an element selected from the group consisting of Li, Na, Mg, Ca, Sr, Fe, Cu, U, B, and mixtures thereof.

The term "phosphate" is employed to define a group of inorganic salts of phosphoric acid wherein one or more of the hydrogen atoms of the acid have been replaced by an element selected from the group consisting of Li, Na, Mg, Ca, Sr, Fe, Cu, U, B and mixtures thereof. The majority of salts of the present invention may be called "normal" phosphates in which all of the hydrogen atoms of the acid have been displaced (Hackh's Chemical Dictionary, 4th edition, McGraw-Hill Book Co., 1969); however, there are other degrees of displacement contemplated and illustrated herein, e.g. uranyl phosphate $UO_2HPO_4$. The double salts, i.e. those wherein the hydrogen atoms are displaced by different members of the group Li, Na, Mg, Ca, Sr, Fe, Cu, U and B are also contemplated in the present invention.

It is theorized, without intending any limitation to the scope of the present invention that the function of the phosphate is at least two-fold in the reaction. First, the phosphate serves to absorb any metal ions in the reaction medium thus reducing the possibility of further oxidation, which may be catalyzed by such stray ions and secondly, in a similar manner the phosphate absorbs acids that are formed, reducing the possibility of side reaction acid catalysis. The phosphate can be used at low concentrations, i.e., as low as 0.025 weight percent based on hydrocarbon feed. Excellent results have been obtained in the 0.05 weight percent range based on the hydrocarbon feed. Generally no more than 0.2 weight percent of the phosphate would be employed and preferably 0.1 or less weight percent. Larger amounts of phosphate can be detrimental to the reaction. It has been observed that there is a decrease in the selectivity of the reaction for hydroperoxides as the conversion is increased in the presence of a given amount of phosphate. The effect on hydroperoxide selectivity can be somewhat mitigated by the use of additional quantities of phosphate. Within the specified ranges one skilled in the art will be able to select the quantity of phosphate for a desired product distribution at a desired economic cost and ease of operation.

The process of the present invention is used for the preparation of hydroperoxides from tertiary alkanes, aralkanes and cycloalkanes. Suitably, the tertiary alkanes and cycloalkanes would have from 3 to 30 carbon atoms, preferably 4 to 10 and most preferably 5 to 8 carbon atoms. The carbons on the tertiary carbon atom may be primary, secondary or tertiary, thus there may be more than one tertiary carbon atom in a compound. Some examples of tertiary alkanes intended to be included are isobutane, isopentane, 2-methyl pentane, 3-methyl hexane, 2,3-dimethyl hexane, 4-methyl heptane, 4-n-propyl heptane, 3-tertiary butyl-hexane, 2-methyl decane, 2,6-dimethyl-3-isopropyl heptane, 2,11-dimethyl dodecane, 2-methyl-heptadecane, 7-isopropyl-hexadecane, 4, -n-propyl-nonadecane, 10-n-nonyl-n-nonadecane and the like. The cycloalkane may be mono, di or tri cyclo, etc. unsubstituted or substituted with hydrocarbons. The hydrocarbon substituent will usually contain 1 to 10 carbon atoms and may be branched or unbranched. Suitable cycloalkanes include for example cyclopropane, propylcyclopropane, 1-methyl-2 (2-methyl propyl) cyclopropyl, cyclobutane, 1,2-dimethylcyclobutane, 1,2-diisopropylcyclobutane, cyclopentane, ethyl cyclopentane, cyclohexane, 1,2,4-trimethyl cyclohexane, propylcycloheptane, cyclooctane, methylcyclooctane, cycloundecane, cyclododecane, cyclooctadecane, cyclotriacontane, cyclopentylcyclopentane, cyclopentylcyclohexylmethane, bicyclohexane, [0,3,3] bicyclooctane, perhydrophenanthrene, 1,3-dimethyl 7-isopropyl-2,3-(3-methyl-cyclohexano) - [0,4,4] -dicyclodecane and the like. The aralkane will generally have one or two aromatic groups and includes, for example, ethyl benzene, cumene, o-cymene, 2-ethyl naphthalene, 2-ethyl-6-methyl naphthalene and the like. A particularly preferred group of hydrocarbons for use in the present process are isobutane, isopentane, isohexane, isoheptane, isooctane, ethyl benzene, cumene, cyclopentane, cyclohexane and cycloheptane.

As stated above the tertiary alkane may contain secondary and other tertiary groups, likewise the aralkane and the cycloalkane can contain various hydrocarbon substituents as well as more than one cyclic structure. Such highly branched and substituted hydrocarbons are generally suitable for the present process, however, it should be borne in mind that presence of more than one tertiary group on the tertiary alkane or the aralkane or the presence of alkyl substituents, particularly tertiary substituents on the cycloalkane, can result in a great profusion of products since the number of principal active sites is increased with each substitution. That is not to say that all of the sites even of the same or similar grouping will possess the same degree of activity. Other factors such as the electron density, steric and kinetic considerations, and the like, may for the most part control such activity. In any event, it should be expected that use of exotic or complex hydrocarbon starting materials will probably give lower selectivities to the desired hydroperoxides. In the present examples such complicating reactions are largely avoided by use of a relatively simple tertiary alkane, i.e., isopentane, which will demonstrate the type of reaction and the advantages that can arise from the present process.

The reactions of the present process result in hydroperoxides corresponding to the starting hydrocarbon. Since the tertiary carbon is the most reactive in the autoxidation, the produt is almost entirely the tertiary hydroperoxide. The secondary carbon atoms in unsubstituted cycloalkanes are similar to the tertiary groups and react accordingly; however, a tertiary carbon is the preferred reaction site in the substituted cycloalkanes. The following examples will demonstrate the reaction: Isobutane to tertiarybutyl hydroperoxide, isopentane to tertiary-amyl hydroperoxide, isohexane to tertiary-hexyl hydroperoxide, ethyl benzene to α-phenyl ethyl hydroperoxide, cyclopentane to cyclopentyl hydroperoxide, decalin to decalin-4'-hydroperoxide.

The present reaction is an autoxidation carried out at somewhat elevated temperatures. Generally the temperatures which are most suitable for the oxidation will be between about 120°–180° C. and more preferably about 140°–160° C. In autoxidations there is usually an induction period during which the reaction proceeds very slowly. During this period the production of hydroperoxide is slow, however, when a sufficient concentration of hydroperoxide is achieved the reaction is initiated as its "real" reaction rate. The induction period can be reduced by the use of high initial temperatures, i.e., 160°–170° C. which will allow the rapid build up of hydroperoxide. However, once the reaction is initiated the temperature can be reduced, e.g., 140°–160° C. Temperatures higher than 180° C. should not be employed after the reaction has been initiated since the possibility of further oxidation of the peroxide is enhanced.

The induction period mentioned above can also be reduced by the addition of an initiator such as some of the hydroperoxide product to be produced. Other initiators are free radical initiators such as α-methyl benzyl hydroperoxide, α-methyl-p-methylbenzenyl hydroperoxide, α-methyl-α'-n-propyl-p-xylylene dihydroperoxide, ethyl acetoacetate, phenylacetone, acetylacetone and the like.

The autoxidation is carried out by contacting the tertiary alkane in liquid phase at the temperatures and conditions set out herein with molecular oxygen. The oxygen can be furnished as pure oxygen or in gases containing oxygen, e.g., air or mixtures of oxygen with inert gases, such as helium or nitrogen in the same or substantially different proportions as oxygen is found in air.

Sufficient pressure is employed so as to maintain the reaction mixture in liquid phase. This will usually require more than atmospheric pressure, although some of the hydrocarbons encompassed herein are liquid at atmospheric pressure at temperatures up to 180° C. Generally, however, pressure will be required. It is not necessary to use any more pressure than is necessary to maintain the liquid phase since oxygen is not believed to be the rate determining factor in the reaction. Pressures of atmospheric up to about 1000 psi will usually be sufficient.

Diluents can be used, for example, benzene, toluene, xylene, naphthalene, tert-butyl alcohol, tert-amyl alcohol, nitrobenzene, carbon tetrachloride, and the like. It should be noted that such diluent will decrease the rate of reaction. Generally, the unreacted feed material will be a sufficient diluent for this reaction. The usual metal oxidation catalysts should not be present during the present reaction and any solvent should be examined to be sure it is free of such contaminants.

In carrying out the process it has been found that the best results are obtained when the phosphate is thoroughly dispersed in the reaction medium. This is best achieved by agitation of the reaction medium, for example, by high speed stirring. An aid to maintaining the dispersion would be the use of very fine powders such as below, about 20 micron size. The phosphate is easily recovered since it is a solid in the reaction system. The presence of residual phosphate in the product is not, however, detrimental but is advantageous in that the phosphates stabilize the hydroperoxides.

The following examples will illustrate the operation of the invention and the advantages to be derived therefrom. The apparatus used in each of the following examples was a 3,000 p.s.i. magnetically stirred, 1.4 liter, stainless steel autoclave, equipped with a Dispersamax agitator, reflux condenser and internal water cooling coil. The isopentane feed, and other materials for the reaction were charged to the reactor. Oxygen containing gas was added continuously with sufficient pressure to maintain the liquid phase. Inlet gas was measured by following the pressure drop in a standardized metering vessel and fed into the autoclave through a ballast type pressure regulator. Exit gas, at atmospheric pressure, was then passed through three dry ice traps, an ascarite trap, a wet test meter and then vented. Pure oxygen was employed in the present examples unless otherwise indicated.

EXAMPLES 1–4

These examples show the use of boron phosphate at .05 wt. % concentration based on hydrocarbon reactant. The reactants, proportion conditions and results are set out in Table I.

TABLE I

OXIDATION OF ISOPENTANE UNDER 600 PSI OXYGEN PRESSURE

| Example No. | 1 | 2 | 3 | 4 Control |
|---|---|---|---|---|
| Reactants | | | | |
| Isopentane, g. | 600 | 600 | 600 | 600 |
| Boron Phosphate g. | 0.3 | 0.3 | 0.3 | — |

TABLE I-continued

OXIDATION OF ISOPENTANE UNDER 600 PSI OXYGEN PRESSURE

| Example No. | 1 | 2 | 3 | 4 Control |
|---|---|---|---|---|
| Reaction Conditions | | | | |
| Temperature, °C. | 150 | 160 | 170 | 140 |
| Total Reaction Time, hrs. | 4.25 | 2.67 | 1.22 | 4.17 |
| Results | | | | |
| Induction Period, min. | 141 | 103 | 41.5 | 176 |
| Oxygen Consumed, mole | 0.966 | 1.067 | 1.052 | 1.098 |
| Carbon Dioxide Produced, Mole | 0.025 | 0.010 | 0.011 | 0.020 |
| Hydroperoxide Concentration, wt. % | 10.60 | 9.49 | 9.06 | 7.98 |
| Isopentane Conversion, % | 9.9 | 8.3 | 8.4 | 10.0 |
| % Selectivity (Mole Product/100 Mole Hydrocarbon Consumed) | | | | |
| Acetone | 18.3 | 14.0 | 19.7 | 31.2 |
| TAA* | 1.5 | 0.6 | 1.5 | 4.8 |
| TAHP** | 75.0 | 80.6 | 76.8 | 56.8 |

*Tertiary amyl alcohol
**Tertiary amyl hydroperoxide

Each run was a different temperature. Even at a 170° C., the selectivity to TAHP remained high while selectivity to acetone remained below 20%. This is important. The acetone by-product is not desirable since it is a lower cost material than the isopentane feed. The higher temperature allows much shorter reaction times.

EXAMPLES 5-13

These runs show a number of the phosphates at two concentrations. Examples 5-9 show the phosphates at 0.05 weight percent based on isopentane. Examples 10-13 show the effect of a 0.2 weight percent of phosphate. At 0.2 wt. % there is a noticeable increase in the selectivity to acetone. For the most part there is no advantage to be gained at phosphate concentrations of greater than 0.2 wt. % and as can be seen from Table II, there are definite disadvantages. The conditions, reactants, proportions and results are set out in Table II,

EXAMPLES 14-16

These examples show some other suitable phosphates at 0.05 wt. % concentration. Conditions, reactants, proportions and results are in Table III.

TABLE III

OXIDATION OF ISOPENTANE UNDER 600 PSI OXYGEN PRESSURE

| Example No. | 14 | 15 | 16 |
|---|---|---|---|
| Reactants | | | |
| Isopentane, g. | 600 | 600 | 600 |
| Cupric Phosphate, g. | 0.3 | — | — |
| Uranyl Phosphate, g. | — | 0.3 | — |
| Strontium Phosphate, g. | — | — | 0.3 |
| Reaction Conditions | | | |
| Temperature, °C. | 140 | 150 | 140 |
| Total Reaction Time, hrs. | 4.50 | 3.33 | 6.80 |
| Results | | | |
| Induction Period, min. | 65 | 84 | 153 |
| Oxygen Consumed, mole | 0.721 | 0.752 | 0.907 |
| Carbon Dioxide Produced, mole | 0.001 | 0.005 | 0.001 |
| Hydroperoxide Concentration, wt. % | 5.09 | 7.04 | 8.17 |
| Isopentane Conversion, % | 4.4 | 6.2 | 9.2 |
| % Selectivity (Mole Product/100 Mole Hydrocarbon Consumed) | | | |
| Acetone | 13.4 | 13.3 | 17.7 |
| TAA | 1.9 | 2.1 | 14.1 |
| TAHP | 81.9 | 80.2 | 63.0 |

EXAMPLES 17-27

These examples demonstrate a number of phosphate compounds similar to those of the present invention which are not suitable catalyst for the preparation of hydroperoxides. These phosphates cause the reactions to go less effectively than the uncatalyzed control run. Conditions, reactants, proportions and results are in Table IV.

TABLE II

OXIDATION OF ISOPENTANE UNDER 600 PSI OXYGEN PRESSURE

| Example No. | 4 | 5 | 6 | 7 | 8 | 9 | 10 | 11 | 12 | 13 |
|---|---|---|---|---|---|---|---|---|---|---|
| Reactants | | | | | | | | | | |
| Isopentane, g. | 600 | 600 | 600 | 600 | 600 | 600 | 100 | 100 | 100 | 600 |
| Sodium Phosphate, g. | — | 0.3 | — | — | — | — | — | — | — | — |
| Magnesium Phosphate, g. | — | — | 0.3 | — | — | — | 0.2 | — | 0.2 | — |
| Lithium Phosphate, g. | — | — | — | 0.3 | — | — | — | — | — | — |
| Ferric Phosphate, g. | — | — | — | — | 0.3 | — | — | — | — | 1.2 |
| Calcium Phosphate, g. | — | — | — | — | — | 0.3 | — | 0.2 | — | — |
| Reaction Conditions | | | | | | | | | | |
| Temperature, °C. | 140 | 140 | 150 | 150 | 150 | 150 | 140 | 140 | 140 | 150 |
| Total Reaction Time, hrs. | 4.17 | 5.37 | 2.83 | 4.33 | 5.00 | 4.07 | 7.33 | 7.67 | 3.13 | 2.67 |
| Results | | | | | | | | | | |
| Induction Period, min. | 176 | 170 | 84.5 | 125 | 143 | 128 | 251 | 244 | 73 | 46 |
| Oxygen Consumed, Mole | 1.098 | 0.990 | 0.927 | 0.981 | 0.847 | 0.967 | 0.242 | 0.182 | 0.226 | 0.985 |
| Carbon Dioxide Produced, Mole | 0.020 | 0.018 | 0.013 | 0.013 | 0.011 | 0.013 | 0.005 | 0.003 | 0.008 | 0.014 |
| Hydroperoxide Concentration, wt. % | 7.98 | 9.60 | 8.19 | 9.59 | 9.71 | 9.99 | 15.21 | 13.10 | 8.98 | 8.93 |
| Isopentane Conversion % | 10.0 | 9.5 | 7.9 | 8.3 | 8.3 | 10.6 | 16.2 | 12.4 | 10.4 | 8.6 |
| % Selectivity (Mole Product/100 Mole Hydrocarbon Consumed) | | | | | | | | | | |
| Acetone | 31.2 | 19.0 | 19.2 | 16.0 | 13.5 | 15.9 | 22.9 | 18.3 | 35.4 | 23.9 |
| TAA | 4.8 | 1.3 | 0.9 | 0.2 | 0.6 | 8.8 | 7.8 | 4.0 | 0.6 | 0.4 |
| TAHP | 56.8 | 72.0 | 73.6 | 80.7 | 81.4 | 67.1 | 67.3 | 75.4 | 64.0 | 73.9 |

TABLE IV

OXIDATION OF ISOPENTANE UNDER 600 PSI OXYGEN PRESSURE

| EXAMPLE No. | Control 4 | 17 | 18 | 19 | 20 | 21 | 22 | 23 | 24 | 25 | 26 | 27 |
|---|---|---|---|---|---|---|---|---|---|---|---|---|
| Reactants | | | | | | | | | | | | | |
| Isopentane, g. | 600 | 600 | 600 | 600 | 600 | 600 | 600 | 600 | 600 | 600 | 600 | 600 |
| Zinc Phosphate, g. | — | — | — | — | — | 0.3 | 0.3 | 0.3 | — | — | — | — |
| Chromium Phosphate, g. | — | 0.3 | 0.3 | — | — | — | — | — | — | — | — | — |
| Potassium Phosphate, g. | — | — | — | 0.3 | — | — | — | — | — | — | — | — |
| 12-Molybdophosphoric Acid, g. | — | — | — | — | 0.3 | — | — | — | — | — | — | — |
| Cupric Borate, g. | — | — | — | — | — | — | — | — | 0.3 | 0.3 | — | — |
| Sodium Molybdophosphate, g. | — | — | — | — | — | — | — | — | — | — | 0.3 | — |

TABLE IV-continued
OXIDATION OF ISOPENTANE UNDER 600 PSI OXYGEN PRESSURE

| EXAMPLE No. | Control 4 | 17 | 18 | 19 | 20 | 21 | 22 | 23 | 24 | 25 | 26 | 27 |
|---|---|---|---|---|---|---|---|---|---|---|---|---|
| Phosphoric Acid, g. | — | — | — | — | — | — | — | — | — | — | 0.3 | 0.04 |
| Reaction Conditions | | | | | | | | | | | | |
| Temperature, °C. | 140 | 150 | 140 | 150 | 150 | 150 | 140 | 140 | 150 | 140 | 150 | 150 |
| Total Reaction Time, hrs. | 4.17 | 2.33 | 3.20 | 2.20 | 2.50 | 2.47 | 2.67 | 3.5 | 2.33 | 4.17 | 2.58 | 3.0 |
| Results | | | | | | | | | | | | |
| Induction Period, min. | 176 | 64 | 105 | 91 | 69 | 103 | 108 | 128 | 114 | 203 | 106 | 93 |
| Oxygen Consumed, Mole | 1.098 | 1.11 | 0.984 | 0.964 | 1.15 | 1.284 | 1.245 | 1.036 | 1.774 | 1.336 | 1.149 | 1.090 |
| Carbon Dioxide Product, Mole | 0.020 | 0.017 | 0.018 | 0.014 | 0.022 | 0.001 | 0.040 | 0.024 | 0.001 | 0.001 | 0.019 | 0.017 |
| Hydroperoxide Concentration, wt % | 7.98 | 7.23 | 5.85 | 7.57 | 2.38 | 6.26 | 3.87 | 5.04 | 4.53 | 6.17 | 4.60 | 7.49 |
| Isopentane Conversion, % | 10.0 | 9.6 | 8.6 | 8.8 | 6.3 | 9.1 | 8.5 | 9.3 | 12.4 | 9.6 | 9.4 | 10.7 |
| % Selectivity (Mole Product/100 Mole Hydrocarbon Consumed) | | | | | | | | | | | | |
| Acetone | 31.2 | 28.4 | 30.9 | 32.8 | 68.4 | 35.7 | 48.2 | 37.7 | 59.0 | 45.8 | 37.1 | 28.1 |
| TAA | 4.8 | 12.5 | 15.1 | 0.7 | 0.8 | 11.4 | 17.3 | 18.6 | 7.5 | 6.2 | 20.5 | 14.3 |
| TAHP | 56.8 | 53.6 | 48.3 | 60.2 | 26.9 | 50.3 | 33.1 | 37.9 | 27.3 | 45.4 | 35.3 | 49.8 |

Generally it would be most preferable to have the highest selectivities to hydroperoxides possible, however, the very nature of the desired product, the hydroperoxide, makes this a difficult task. The present process does provide for startlingly high hydroperoxide selectivities at reasonable conversion rates. The loss in selectivity for hydroperoxides is picked up by other products, e.g., predominately the ketone and alcohol (other possible by-products include aldehydes, acids, $CO_2$, $CO$ and $H_2O$). The phosphates of the invention tend to suppress rapid increases for ketone. Ketones can be valuable by-products but are more commonly problems. The ketone is, of course, the result of the degradative oxidation of the hydroperoxide. Thus, there is a scission in the carbon chain, meaning that for every mole of ketone there is a mole of yet another by-product. The alcohol on the other hand is an excellent diluent for the hydroperoxide. Compositions comprising principally hydroperoxides and alcohol (in a hydrocarbon diluent, i.e., the starting material) can be used directly in other processes. For example, a process described in U.S. Pat. No. 3,351,635 uses a solution of a hydroperoxide (prepared in liquid phase by autoxidation) in hydrocarbon, along with some of the alcohol formed during the oxidation, to form oxirane compounds by reaction with an olefinically unsaturated compound. The highly reactive ketones are a detriment to a process such as that disclosed in U.S. 3,351,635 and other similar reactions where the alcohol can be tolerated.

The alcohols as such are quite valuable since they are easily dehydrated by conventional means to the corresponding olefins.

In addition to serving as reactants the organic hydroperoxides are excellent free radical initiators and their use for this purpose being well known and widespread.

The hydroperoxides can be concentrated by conventional means such as neat crystallization, distillation or extraction. Those familiar with hydroperoxides are aware of their tendency on occasions to undergo violent decomposition and the usual safety measures should be taken for personnel and equipment.

The invention claimed is:

1. A process for preparing organic hydroperoxides comprising contacting a hydrocarbon selected from at least one of the group consisting of isobutane, isopentane, isohexane, isoheptane, ethylbenzene, cumeme, cyclopentane, cyclohexane, cycloheptane, cyclooctane and cyclooctadecane with molecular oxygen in liquid phase at a pressure from about atmospheric up to about 1000 psi and at a temperature from about 120 to 180° C. in the presence of an inorganic phosphate salt of phosphoric acid wherein one or more of the hydrogen atoms of the acid have been replaced by an element selected from the group consisting of Fe, Cu, U, and mixtures thereof, the said phosphate salt being present in an amount of from about 0.025 to 0.2 weight percent based on the hydrocarbon feed.

2. The process according to claim 1 wherein the temperature is between 140–160° C.

3. The process according to claim 2 wherein the pressure is sufficient to maintain the liquid phase.

4. The process according to claim 3 wherein the hydrocarbon is selected from the group consisting of isobutane, isopentane, isohexane, isoheptane, isooctane, ethylbenzene, cumene, cyclopentane, cyclohexane and cycloheptane.

5. The process according to claim 4 wherein the hydrocarbon is isopentane and the hydroperoxide is tertiary amyl hydroperoxide.

6. The process according to claim 5 wherein the phosphate salt is ferric phosphate.

7. The process according to claim 5 wherein the phosphate salt is cupric phosphate.

8. The process according to claim 5 wherein the phosphate salt is uranyl phosphate.

9. The process according to claim 1 wherein the said phosphate salt is present in an amount of 0.1 or less weight percent based on the weight of the hydrocarbon.

10. A process for the preparation of tertiary amyl hydroperoxide comprising contacting isopentane with molecular oxygen in the liquid phase at a pressure of from about atmospheric to 1000 psi and at a temperature of from 120 to 180° C. in the presence of from 0.025 to 0.1 percent by weight of an inorganic phosphate salt of phosphoric acid wherein one or more of the hydrogen atoms of the acid have been replaced by an element selected from the group consisting of Fe, Cu, U, and mixtures thereof.

11. The process according to claim 10 wherein the phosphate salt is ferric phosphate.

12. The process according to claim 10 wherein the phosphate salt is cupric phosphate.

13. The process according to claim 10 wherein the phosphate salt is uranyl phosphate.

* * * * *